United States Patent [19]
Mount et al.

[11] 3,965,339
[45] June 22, 1976

[54] APPARATUS AND METHOD FOR MEASURING HEART CONDITION

[75] Inventors: Bruce E. Mount, Diamond Bar; James R. Barela, Duarte, both of Calif.

[73] Assignee: City of Hope-A National Medical Center, Los Angeles, Calif.

[22] Filed: Apr. 3, 1975

[21] Appl. No.: 564,798

[52] U.S. Cl. .......................... 235/151.3; 128/2.05 R
[51] Int. Cl.² ....................... G06G 7/60; A61B 5/02
[58] Field of Search ................. 235/151.3, 183, 196; 128/2.05 R, 2.05 D, 2.05 E, 2.05 F, 2.05 Q, 2.06 G, 2.1 R

[56] References Cited
UNITED STATES PATENTS

| 3,087,488 | 4/1963 | Streimer | 128/2.05 |
|---|---|---|---|
| 3,304,413 | 2/1967 | Lehmann et al. | 235/92 |
| 3,556,082 | 1/1971 | McCullough | 128/2.05 |
| 3,563,661 | 2/1971 | Charlson et al. | 235/151.3 |
| 3,566,092 | 2/1971 | Grant et al. | 235/151.3 |
| 3,651,318 | 3/1972 | Czekajewski | 235/183 |
| 3,720,818 | 3/1973 | Spragg et al. | 235/151.3 |
| 3,831,590 | 8/1974 | Boyle et al. | 128/2.05 R |

OTHER PUBLICATIONS

G. D. Buckberg et al., "Experimental Subendocardial Ischemia in Dogs with Normal Coronary Arteries," *Circulation Research*, vol. XXX, Jan. 1972, pp. 67–81.

*Primary Examiner*—Malcolm A. Morrison
*Assistant Examiner*—Jerry Smith
*Attorney, Agent, or Firm*—Harris, Kern, Wallen & Tinsley

[57] ABSTRACT

Apparatus and method for continuous measurement and display of the endocardial viability ratio of a patient to provide an indication of the condition of the heart muscle. A system using signals representative of the systemic arterial pressure and the left atrial pressure as inputs to generate a tension time index and a diastolic pressure time index by separation of the systemic arterial pressure wave form into two parts and selective integration of the inputs, followed by division to obtain the desired ratio.

8 Claims, 4 Drawing Figures

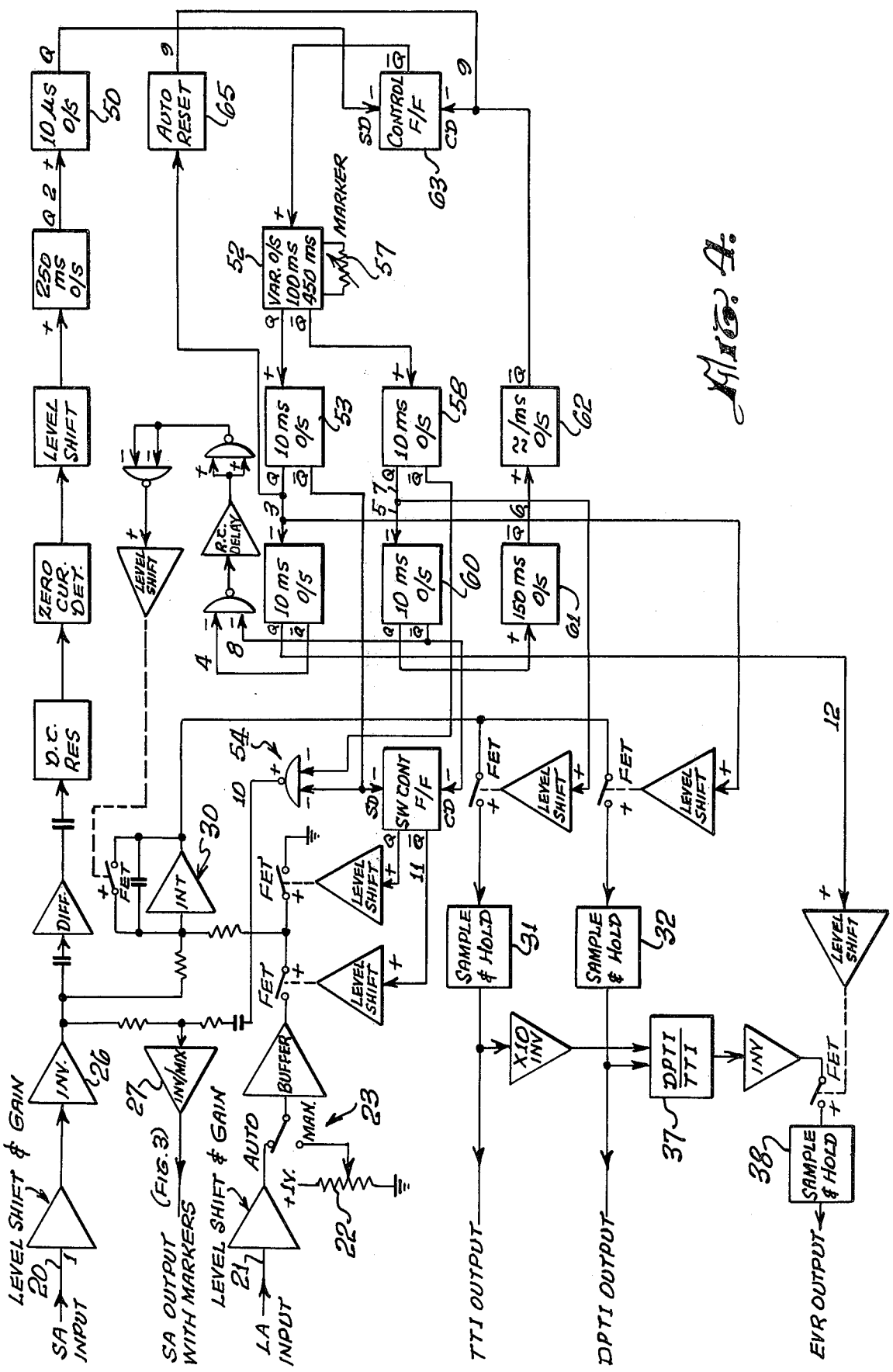

3,965,339

APPARATUS AND METHOD FOR MEASURING HEART CONDITION

BACKGROUND OF THE INVENTION

This invention relates to apparatus and method for providing information on the condition of the heart muscle, particularly during post-operative care following open heart surgery. It has been determined that the endocardial viability ratio is related to a heart condition of significant interest. See the article in Circulation Research Volume XXX, January 1972, pages 67-81, Experimental Subendocardial Ischemia in Dogs with Normal Coronary Arteries, by Buckberg et al. In the work described in the article, certain conditions were produced in the heart, measurements were taken and recorded, various calculations were then made to obtain various data including the endocardial viability ratio (EVR), the muscle was examined, and the conclusions were drawn relating muscle condition to EVR.

This is a time-consuming and laborious process, and it is an object of the present invention to provide a new and improved apparatus and method for obtaining the EVR instantaneously and continuously so that heart conditions can be monitored and appropriate procedures initiated as required.

SUMMARY OF THE INVENTION

The patient's systemic arterial pressure (SA) and left atrial pressure (LA) are measured using conventional pressure transducers to provide electrical signals. In an alternative form, an adjustable voltage source may be used in lieu of an LA transducer, with the voltage output set to a value representative of the LA pressure. The SA wave form is displayed on an oscilloscope with a first marker at the onset or leading edge of the pressure wave and a second marker at the dicrotic notch. The first marker is automatically generated at the onset, while the second marker is manually varied to position it at the notch. The SA wave form is integrated over the time from the first marker to the second marker to provide a tension time index (TTI). The difference between the SA wave form and the LA wave form is integrated over the period from the second marker to the next first marker to provide a diastolic pressure time index (DPTI). Sample and hold circuits are provided for the integrator output to obtain the TTI and DPTI outputs. A dividing circuit is provided to obtain the ratio of the indexes, typically DPTI divided by TTI, which ratio is the desired EVR. Aortic assist or other circulatory assist pumps are often used in post-operative care and a delay circuit is introduced into the equipment to prevent false indications resulting from pump operation.

BRIEF DESCRIPTION OF THE DRAWINGS

FIG. 4 is a logic diagram for the apparatus of FIG. 1.

DESCRIPTION OF THE PREFERRED EMBODIMENT

Figure 1:
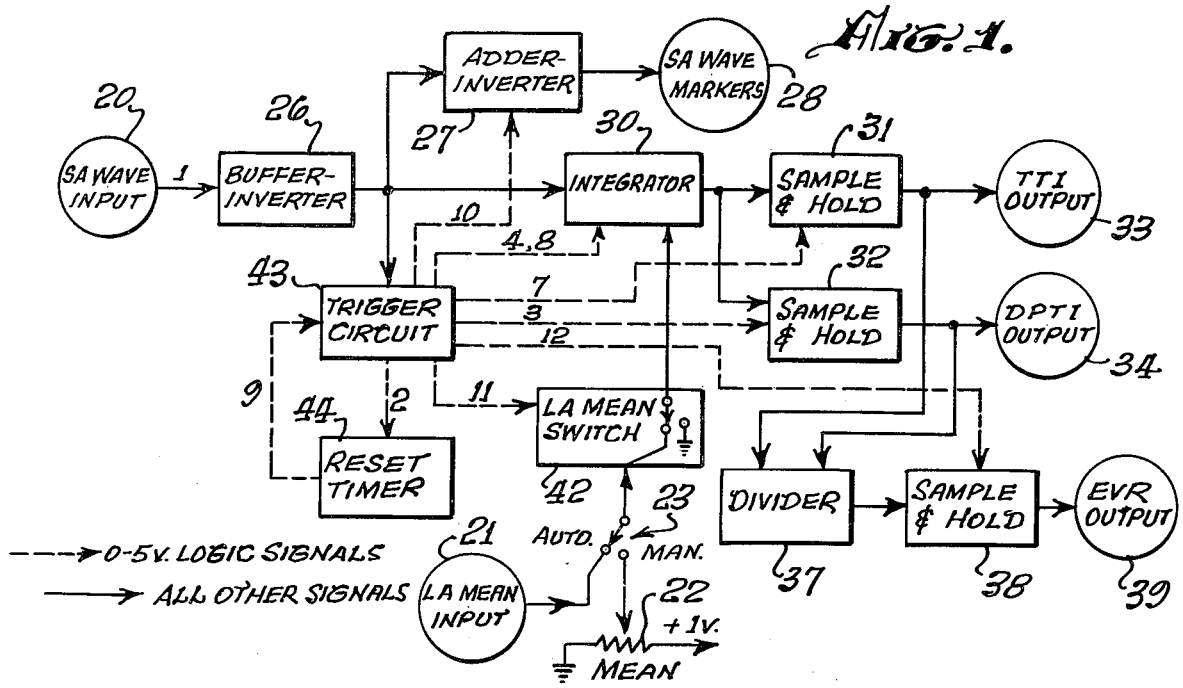
FIG. 1 is a block diagram of an apparatus for indicating heart condition and incorporating the presently preferred embodiment of the invention.

The instrument of FIG. 1 includes an input terminal 20 for the SA signal and another terminal 21 for the LA signal. The SA signal may be obtained in the conventional manner, as by introducing a catheter into an artery and coupling the catheter to a pressure transducer for generating the electrical signal. Similarly, the LA signal may be obtained by introducing a catheter into the left atrium and coupling it to another pressure transducer. Since the LA pressure changes slowly, the central venus pressure may be utilized in lieu of a direct measurement of the pressure in the left atrium. As another alternative, an estimate for the LA pressure can be utilized, with the LA signal obtained from a potentiometer 22 connected across a voltage source. The potentiometer pointer is manually set to provide the desired signal value, and a switch 23 permits the operator to select either the signal at terminal 21 or the signal at the potentiometer 22.

The SA signal is connected through a buffer 26 and an adder 27 to a display unit 28, typically a cathode ray oscilloscope. The wave forms at various points in the diagrams of FIGS. 1 and 4 are illustrated in FIG. 2, with the wave forms and positions in the instrument indicated by the numerals 1-12.

Figure 2:
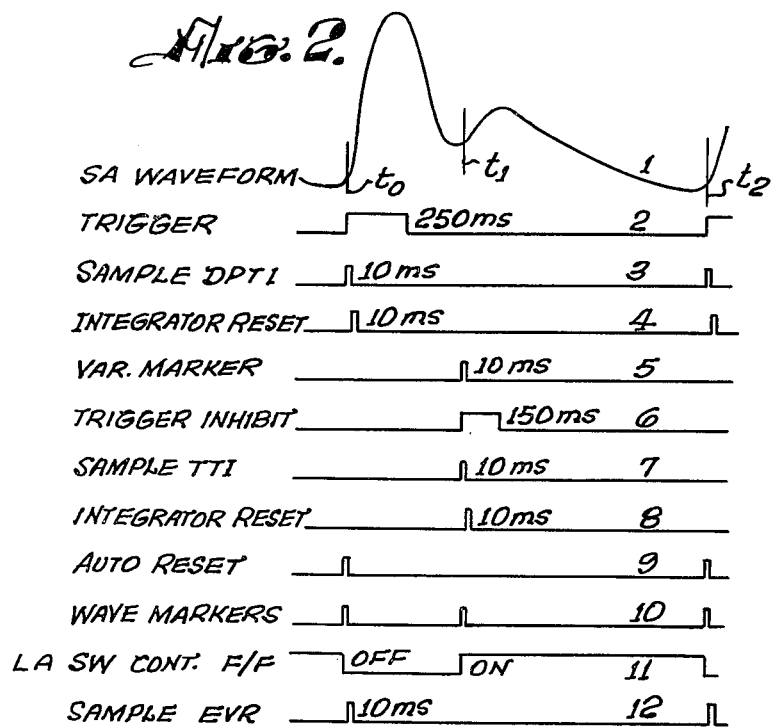
FIG. 2 is a timing diagram illustrating the operation of the apparatus of FIG. 1.
Figure 3:
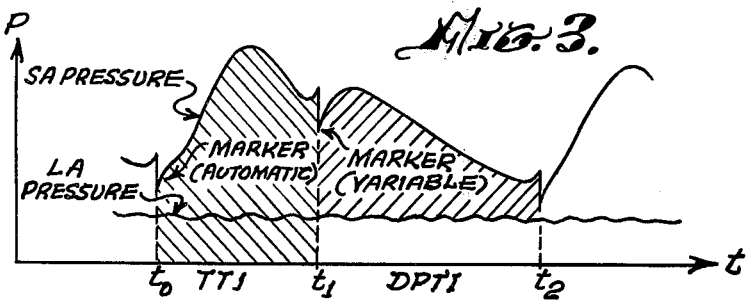
FIG. 3 illustrates a typical display of the apparatus of FIG. 1.

As shown in FIG. 2 and in FIG. 3, the SA pressure wave has an onset or leading edge at $t_0$ and a minimum or dicrotic notch at $t_1$, with the wave repeating with another onset at $t_2$. This SA wave with pulse markers (to be described) is displayed on the oscilloscope 28 for continuous viewing by the operator.

The SA wave from the buffer 26 is also connected to an integrator 30, with the integrator output connected to sample and hold units 31 and 32. The output from the unit 31 is connected to a display, such as a meter 33 and the output of unit 32 is connected to another display such as a meter 34. The outputs of units 31 and 32 are also connected to a divider 37, with the divider output connected to another sample and hold unit 38 which in turn is connected to another display such as a meter 39. The LA signal is connected through the switch 23 and another switch 42 to the integrator 30.

The operation of the integrator, the sample and hold units, and the switch 42 is controlled by timing pulses from a trigger circuit 43, with the interconnections shown by the dashed lines. The marker pulses at $t_0$ and $t_1$ for the display of the SA wave are also generated by the trigger circuit 43. The device is reset by a reset timer 44 interconnected with the trigger circuit 43.

In operation, the SA signal source is connected to terminal 20 and the LA signal source, if used, is connected to terminal 21, with switch 23 in the automatic position. Alternatively, the potentiometer 22 may be set to the position representing the LA signal value and the switch 23 set to the manual position. The SA wave form is now displayed on the oscilloscope 28. The onset marker at $t_0$ and $t_2$ is automatically generated in the trigger circuit 43 by sensing the onset of the leading edge of the wave.

The marker for time $t_1$ is also generated in the trigger circuit 43, with the time of occurrence being manually controlled by the operator (by means of a potentiometer 57 shown in FIG. 4). The operator adjusts the position of the $t_1$ marker by visually inspecting the wave form on the display and turning an adjustment knob to position the $t_1$ marker at the dicrotic notch.

During the period $t_0 - t_1$, the SA wave is integrated in the integrator 30 and the integrator output is sampled by the sample and hold unit 31 at time $t_1$. The sampling is produced by the pulse on line 7, and the integrator is immediately reset by the pulse on line 8. The sampled integrator value is the tension time index TTI and may be read at the meter 33.

During the time $t_1 - t_2$, the LA signal is also connected to the integrator by the switch 42, with the polarities of the SA and LA signals such that the integrator operates on the difference between the SA and LA signals. The integrator output is sampled at $t_2$ by sample and hold unit 32, acting under control of the pulse on line 3, with this sampled value displayed at meter 34 as the diastolic pressure time index DPTI. The integrator is then reset by the pulse via line 4.

The sampled values at units 31 and 32 are divided at the divider 37 to provide a ratio, preferably the ratio of DPTI to TTI. The divider output is sampled immediately after the DPTI sampling, under the control of the pulse on line 12, with the ratio displayed at meter 39. This ratio is the desired endocardial viability ratio EVR, and is continuously available for viewing by the doctor or attendant, providing a continuous on-time measurement and display of EVR.

The operation of the integrator is illustrated in FIG. 3, with the SA signal integrated from $t_0 - t_1$ to provide TTI, and with the difference between the SA signal and the LA signal integrated from $t_1 - t_2$ providing DPTI.

A complete logic diagram for the apparatus of FIG. 1 is given in FIG. 4. The $t_0$, $t_2$ pulse marker is generated by the 10 millisecond one-shot or monostable multivibrator 53 and is connected to the adder 27 through gate 54. The variable marker $t_1$ is generated in the variable one-shot 52, with the timing controlled by variable resistor 57. This variable marker is coupled to the adder 27 through another 10 millisecond one-shot 58 and the gate 54.

A device known as a balloon pump is often utilized in the heart for aiding the heart during the post operative period. The balloon pump is actuated during a certain portion of the heart cycle to close off the descending aorta thereby forcing additional blood into the coronary arteries and upward into the brain. Actuation of the balloon pump produces an onset in the SA pressure wave at a time shortly after the dicrotic notch. In order to prevent this onset from being treated by the apparatus as the onset at $t_2$, operation is blocked for a period of 150 milliseconds after generation of the $t_1$ marker. This is accomplished by the 150 millisecond one-shot 61, the 1 millisecond one-shot 62, and control flip-flop 63. The control flip-flop 63 is cleared by the automatic reset circuit 65. If no sample DPTI pulse 3 occurs within 3 seconds, the reset circuit 65 provides a pulse 9 to clear the flip-flop 63 to accept a pulse from the one-shot 50.

We claim:

1. In an apparatus for continuously measuring the endocardial viability ratio of a patient for use with sources providing electrical signals representing the patient's systemic arterial pressure and left atrial pressure, the improvements comprising in combination:

a first input for a first signal varying as a function of the systemic arterial pressure and having a wave form with a leading edge at time $t_0$, a dicrotic notch at time $t_1$, and another leading edge at time $t_2$;

a second input for a second signal varying as a function of the left atrial pressure;

pulse generator means having said first signal as an input for generating a first pulse at times $t_0$ and $t_2$ and for generating a second pulse at a variable time after $t_0$;

display means for displaying said first signal and said first and second pulses, said pulse generator means including means for adjusting the timing of said second pulse to occur at time $t_1$;

an integrator having said first signal as an input;

a switching circuit for connecting said second signal to said integrator as an input during the time period $t_1$ to $t_2$ in subtractive relation with said first signal;

first and second sample and hold units;

means for connecting said integrator output to said first sample and hold unit for the time period $t_0$ to $t_1$;

means for connecting said integrator output to said second sample and hold unit for the time period $t_1$ to $t_2$; and dividing means having the output of said first and second sample and hold units as inputs for producing the ratio thereof as an output.

2. An apparatus as defined in claim 1 including:

a third sample and hold unit;

means for periodically connecting said dividing means output to said third sample and hold unit; and an indicator having said third sample and hold unit output as an input for continuously indicating the endocardial viability ratio.

3. An apparatus as defined in claim 2 including:

a second indicator having said first sample and hold unit output as an input for continuously indicating the tension time index of the patient; and a third indicator having said second sample and hold unit output as an input for continuously indicating the diastolic pressure time index of the patient.

4. An apparatus as defined in claim 1 including a voltage source connected to said second input as said second signal, with the output of said voltage source being manually variable to represent a mean left atrial pressure.

5. An apparatus as defined in claim 1 including:

delay means for blocking operation of said pulse generator means for a predetermined period of time; and means for connecting said second pulse to said delay means to initiate said predetermined period of time.

6. An apparatus as defined in claim 1 including means for connecting said second input to a left atrial pressure sensor.

7. An apparatus as defined in claim 6 including means for connecting said first input to a systemic arterial pressure sensor.

8. An apparatus as defined in claim 1 including delay means for blocking display of said first pulse for a predetermined time after said second pulse.

* * * * *